US006683191B2

(12) United States Patent
Deng et al.

(10) Patent No.: US 6,683,191 B2
(45) Date of Patent: Jan. 27, 2004

(54) METHOD FOR SYNTHESIS OF SUBSTITUTED AZOLE LIBRARIES

(75) Inventors: Yijun Deng, North Wales, PA (US); Dennis Hlasta, Doylestown, PA (US)

(73) Assignee: Ortho-McNeil Pharmaceuticals, Inc., Raritan, NJ (US)

( * ) Notice: Subject to any disclaimer, the term of this patent is extended or adjusted under 35 U.S.C. 154(b) by 243 days.

(21) Appl. No.: 09/862,741

(22) Filed: May 22, 2001

(65) Prior Publication Data

US 2002/0077483 A1 Jun. 20, 2002

Related U.S. Application Data

(60) Provisional application No. 60/209,730, filed on Jun. 5, 2000.

(51) Int. Cl.[7] ............................................. C07D 233/54
(52) U.S. Cl. ................................ 548/335.1; 548/346.1; 548/309.7; 548/146
(58) Field of Search ........................ 435/7.1; 546/269.7; 548/335.1, 262.2, 202, 235, 346.1, 309.7; 530/334

(56) References Cited

FOREIGN PATENT DOCUMENTS

| WO | WO 9909017 | 2/1999 |
| WO | WO 9931507 | 6/1999 |
| WO | WO 0025768 | 5/2000 |

OTHER PUBLICATIONS

Janda, K. D. "Tagged versus untagged libraries: Methods for the generation and screening of combinatorial chemical libraries" Proc. Natl. Acad. Sci. Nov. 1994, vol. 91 pp. 10779–10785.*
Yan, B.; Gremlich, H. –U. J. Chromatogr. B: Biomed. Sci. Applic. 1999, 725, 91–102.*
Hoekstra, W. J.; Greco, M. N.; Yabut, S. C.; Hulshizer, B. L.; Maryanoff, B. E. "Solid–Phase Synthesis via N–Terminal Attachment to the 2–Chlorotrityl Resin" Tetrahedron Letters 1997, 38(15), 2629–2632.*
Moore, M.; Norris, P. "Dipolar Cycloaddition Reactions on a Soluble Polymer–Supported Dipolarophile: Synthesis of Sugar–derived Triazoles" Tetrahedron Letters 1998, 39, 7027–7030.*
Aryl Ketones as Novel Replacements for the C–Terminal Amide Bond of Succinyl Hydorxamate MMP Inhibitors; George S. Sheppard, Biorganic & Medicinal Chemistry Letters, (1998) 3251–3256.
Pharmacological Study of a Series of α–Aminoacetanilides With Local Anesthetic Activity; M. Colombo, Farmacol Clinical Exp. (1987) 41–47.
(Methoxyalkyl) thiazoles: A New Series of Potent, Selective, and Orally Active 5–Lipoxygenase Inhibitors Displaying High Enantioselectivity; T. Geoffrey, J. Medical Chemistry (1991) 2176–2186.

Formulation of α-(10Methyl-2–Benzimidazolyl) Benzyl Benzoate By the Combined Action of Aromatic Aldehydes and Acyl Halides on l–Methylbenzimidazole; B.I. Khristich; literature cited 1136–1137.

The Thermal condensation of Imidazoles with Carbonyl Compounds; A.M.Roe; Smith–Kline and French Research Institute (1959, 1934) 2195–2200.

Reactions of Imidazoles with Isocyanates at Elevated Temperature, Elefthherios P.Papadopoulos; (1977) Department of Chemistry, University of New Mexico, 3925–3929.

Reactions of Azolels with Isocyanates at Elevated Temperature, Eleftherios P. Papadopoulos; Department of Chemistry, University of New Mexico, (1978) 99–104.

Organosilicon Compounds XV. Cleavage of the Silicon–Carbon Bond of 2–Trimethylsilyl–1–methylimidazole and 2–Trimethylsilyl–1–methylbenzimidazole: Frank H. Pinkerton; Department of Polymer Science, University of Southern Mississippi (1971) 67–72.

Synthesis of (Trimethylily)thiazoles and Reactions with Carbonyl Compounds, Selectively Aspects and Synthetic Utility. Alessandro Dondoni. University of Italy (1987) 1748–1761.

PCT International Search Report, PCT/US01/16719, May 23, 2001.

* cited by examiner

Primary Examiner—Bennett Celsa
Assistant Examiner—Jon D. Epperson

(57) ABSTRACT

The invention relates to methods of synthesizing libraries of diverse and complex 2-substituted azole compounds of the general formula (I) or (II)

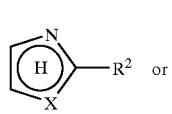

(I)

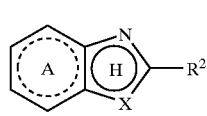

(II)

wherein X, $R^2$ and the ring components

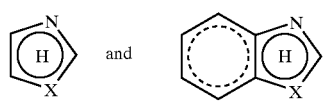

are as described herein, novel intermediates useful for synthesizing such substituted azole compounds and methods for identifying and isolating the compounds.

3 Claims, No Drawings

METHOD FOR SYNTHESIS OF SUBSTITUTED AZOLE LIBRARIES

CROSS REFERENCE TO RELATED APPLICATION

This application claims the priority of U.S. provisional application serial No. 60/209,730 filed Jun. 5, 2000, the contents of which are hereby incorporated by reference.

FIELD OF THE INVENTION

The present invention is directed to a method of synthesizing libraries of diverse and complex 2-substituted azole derivatives and novel intermediate compounds. The invention is further directed to methods for synthesizing the libraries on solid supports.

BACKGROUND OF THE INVENTION

Compounds having biological activity can be identified by screening diverse collections of compounds (i.e., libraries of compounds) produced through synthetic chemical techniques.

The generation of chemical libraries on and off solid resins have proven to be a valuable resource for the pharmaceutical industry in their endeavors to discover new drugs using high throughput screening (HTS) techniques. In creating the libraries, the compounds are ideally synthesized in situ in solution phase or on a solid support. However, relatively simple synthetic methods to produce a diverse collection of such derivatives in situ are often not available.

Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labeled receptor bound to the substrate with its location on the substrate identifies the binding compound. Using these techniques, the development of efficient high throughput screening has greatly enhanced the pharmaceutical industry's ability to screen large numbers of compounds for biological activity.

Central to these methods is the screening of a multiplicity of compounds in the library and the ability to identify the structures of the compounds that have a requisite biological activity. Preferably, in order to facilitate synthesis and identification, the compounds in the library are typically formed on solid supports wherein the compound is covalently attached to the support via a cleavable or noncleavable linking arm. In this regard, libraries of diverse compounds are prepared and then screened to identify "lead compounds" having good binding affinity to the receptor.

Pharmaceutical drug discovery relies heavily on studies of structure-activity relationships wherein the structure of "lead compounds" is typically altered to determine the effect of such alteration on activity. Alteration of the structure of the lead compounds permits evaluation of the effect of the structural alteration on activity.

Thus, libraries of compounds derived from a lead compound can be created by including derivatives of the lead compound and repeating the screening procedures. In this manner, compounds with the best biological profile, i.e., those that are most active and which have the most ideal pharmacologic and pharmacokinetic properties, can be identified from the initial lead compound.

Recently, 2-substituted oxazoles were found to be potent as MMP inhibitors (Sheppard, et al, in *Bioorg Med Chem Lett* 8(22), 3251 (1998)); 2-substituted imidazoles were found to produce local anesthetic effects (Colombo, et al., *Rev Farmacol Clin Exp,* 4(1), 41–47 (1987); and 2-substituted thiazoles were found to be selective inhibitors of 5-lipoxygenase (Bird, et al., 5th *Int Conf Inflamm Res Assoc* (September 23–27 Whit Haven) Abst 85, 1990).

Synthesis of substituted nitrogen containing heteroaryls using solution phase chemistry has been previously described. Khristich et al., in *Khimia Geterotsiklicheskikh Soedineii,* 8, 1136–36 (1983) describe the solution phase synthesis of α-(1-methyl-2-benzimidazolyl)benzyl benzoates. Roe et al., in *JCS* p 2195 (1963) describe the thermal condensation of imidazoles with carbonyl compounds. Papadopolous, in *J. Org. Chem.,* 42 (24) 3925–29, (1977) describes reaction of imidazoles with isocyanates, while Papadopolous et al., in *J. Org. Chem.,* 44(1) 99–104 (1979) describe reactions of azoles with isocyanates. Cleavage of the silicon-carbon bond of 2-trimethylsilyl-1-methylimidazole and 2-trimethylsilyl-1-benzimidazole to yield 2-substituted imidazoles and 2-substituted benzimidazoles is described by Pinkerton, F. H. and Thames, S. F., in *J. Heterocycl. Chem.* 9(1), 67–72 (1972). Dondoni et al., in *J. Org. Chem.,* 53, 1748–61 (1988) describe the synthesis of (trimethylsilyl)thiazoles which are reacted with carbonyl compounds to prepared highly substituted thiazoles.

These methods however, do not permit for rapid synthesis of large libraries with diverse substitution patterns. Thus there exists a need for a solid phase method for synthesis of highly substituted azole compounds.

Accordingly, in order to develop new pharmaceutical drugs to treat various disease conditions, it would be highly desirable to be able to generate such libraries of substituted azole derivatives and novel intermediate compounds optionally attached to a solid support. Thus, there is a need for a facile in situ method for the generation of a multiplicity of substituted azole derivatives and novel intermediate compounds.

SUMMARY OF THE INVENTION

The present invention is directed to a process for assembly of diverse, 2-substituted azole derivatives and novel intermediate compounds using available azoles as starting materials. The rapid synthesis of such highly complex drug-like molecules is unexpected and surprising.

Accordingly, the invention is directed to a method of synthesizing highly substituted azole derivatives having the formula (I) or (II):

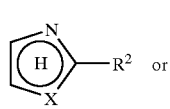
(I)

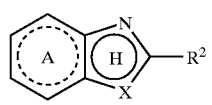
(II)

wherein
X is selected from the group consisting of NH, $NR^A$ and S;

represents a 5 membered aromatic ring structure; optionally containing one to two additional heteroatoms selected from the group consisting of N, O and S;

provided that the additional heteroatoms are not at the attachment point of the R² group (i.e. the R² group is always attached to a ring carbon);

provided that the 5 membered ring remains aromatic in nature;

wherein the 5 membered ring is optionally substituted with one to three substituents independently selected from the group consisting of halogen, hydroxy, alkyl, alkenyl, halogenated alkyl, cycloalkyl, alkoxy, aryl, aralkyl, heterocyclyl, amino, mono-or di-substituted amino, cyano, nitro, —COOR, —COR, —SO₂R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

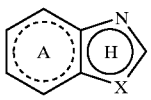

represents a 9 membered ring structure, wherein the five membered portion of the ring structure—

— is aromatic and the six membered portion of the ring structure —

— is saturated, partially unsaturated, or aromatic;

wherein the 5 membered portion of the ring structure is optionally substituted with one to two substituents independently selected from the group consisting of halogen, hydroxy, alkyl, alkenyl, halogenated alkyl, cycloalkyl, alkoxy, aryl, aralkyl, heterocyclyl, amino, mono-or di-substituted amino, cyano, nitro, —COOR, —COR, —SO₂R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent is independently selected from halogen, hydroxy, alkyl, halogenated alkyl, alkoxy, amino, mono-or di-substituted amino, cyano or nitro;

wherein the 6-membered portion of the ring structure may further optionally containing one to four additional heteroatoms selected from the group consisting of N, O and S;

wherein the 6-membered portion of the ring structure may further be optionally substituted with one to four substituents independently selected from the group consisting of halogen, hydroxy, alkyl, halogenated alkyl, cycloalkyl, alkoxy, aryl, aralkyl, heterocyclyl, amino, mono-or di-substituted amino, cyano, nitro, —COOR, —COR, —SO₂R and —CONR$^B$R$^C$; wherein the amine substituents are independently selected from alkyl, cycloalkyl, aryl or aralkyl; wherein the cycloalkyl, aryl or heterocyclyl may be further optionally substituted with one or more substituent independently selected from halogen, hydroxy, alkyl, halogenated alkyl, alkoxy, amino, mono-or di-substituted amino, cyano or nitro;

R² is selected from the group consisting of

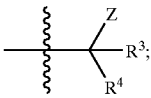

Z is selected from the group consisting of hydrogen, —OH, —OR, —NR$^A$R$^B$, N(R$^A$)OR$^B$, —SR, —CN, —N₃, and

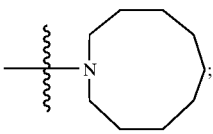

wherein

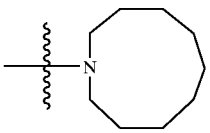

represents a three to eight membered heterocyclyl group bound at the N atom, wherein the heterocyclyl group is saturated, partially unsaturated or aromatic; when the heterocyclyl group is a saturated six to eight membered heterocyclyl, the heterocyclyl group may optionally contains a group selected from O, CHR, NR, S, SO, or SO₂, provided that that the group is separated from the N atom by at least two carbon atoms; and wherein the heterocylcyl group is optionally substituted with one or more substituents independently selected from R;

R³ is selected from the group consisting of hydrogen, alkyl, aralkyl, cycloalkyl, fluorinated alkyl, —COR, —COOR and —CONR$^B$R$^C$; wherein the aralkyl may be optionally substituted with one or more substituents independently selected from halogen, hydroxy, alkyl, halogenated alkyl, alkoxy, amino, mono- or di-substituted amino, cyano or nitro;

R⁴ is selected from the group consisting of alkyl, aryl, aralkyl, cycloalkyl, fluorinated alkyl, alkenyl, alkynyl, —COOR, —COR, —CONCND, -alkyl-COOR, heterocycle and

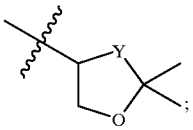

wherein the alkyl, alkenyl, alkynyl, aryl, aralkyl or heterocycle may be optionally substituted with one or more substituents independently selected from halogen, hydroxy, alkyl, halogenated alkyl, aryl, alkoxy, aryloxy, amino, mono-or di-substituted amino, cyano or nitro; wherein Y is selected from the group consisting of O, S and NR$^A$;

where R is selected from the group consisting of alkyl, aryl, aralkyl, cycloalkyl, fluorinated alkyl and heterocycle; wherein the alkyl, aryl, aralkyl or heterocycle may be optionally substituted with one or more substituents independently selected from halogen, hydroxy, alkyl, halogenated alkyl, alkoxy, amino, mono-or di-substituted amino, cyano or nitro;

where $R^A$ is selected from the group consisting of hydrogen, —R, —COOR, —COR, —SO$_2$R and —CONR$^B$R$^C$ and

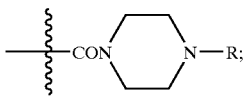

where $R^B$ and $R^C$ are independently selected from the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono-or di-substituted amino, cyano or nitro; or are joined together to form a 4 to 8 membered heterocyclyl ring structure;

which method comprises:

a) preparing a compound of the formula (III) or (V) on a solid support resin,

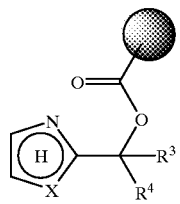
(III)

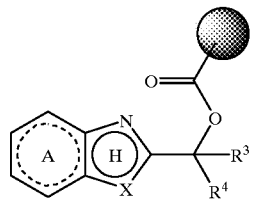
(V)

wherein $R^3$ and $R^4$ are as described above;

b) cleaving the compound from the solid support resin by nucleophilic substitution to yield the corresponding compound of formula (I) or (II);

c) optionally further substituting the compound of formula (I) or (II) via alkylation reactions in solution phase.

DETAILED DESCRIPTION OF THE INVENTION

As used herein, the term "alkyl" whether used alone or as part of a substituent group, shall denote straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1 to 4 carbon atoms. Similarly, as used herein, the term "alkenyl", whether used alone or as part of a substituent group, shall denote straight and branched chain alkene radicals, i.e. straight of branched chains containing at least one double bond. For example, alkenyl radicals include allyl, vinyl, and the like. Similarly, as used herein, the term "alkynyl", whether used alone or as part of a substituent group, shall denote straight and branched chain alkyne radicals, i.e., straight or branched chains containing at least one triple bond. For example, alkynyl radicals include —CCH, —CH$_2$CCH (propargyl), —CH$_2$CCCH$_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, "halogen" shall mean chlorine, bromine, fluorine and iodine.

As used herein, unless otherwise noted, "aryl" shall refer to carbocyclic aromatic groups such as phenyl, naphthyl, and the like. Similarly, the term "aryloxy" shall denote the oxygen ether radical of the above described aryl group, i.e. —O-(aryl). Suitable examples include phenyloxy, naphthyloxy, and the like.

As used herein, unless otherwise noted, "aralkyl" shall mean any lower alkyl group substituted with an aryl group such as phenyl, naphthyl and the like. Suitable examples of aralkyls include benzyl, 1-(phenyl)ethyl, naphthylmethyl, and the like.

As used herein, the term "cycloalkyl" shall denote any monocyclic three to eight membered, saturated carbocyclic ring structure. Suitable examples include cyclopropyl, cyclobutyl, cyclopentyl, cyclohexyl, cycloheptyl and cycloocytyl.

As used herein, unless otherwise noted, the terms "heterocycle", "heterocyclyl" and "heterocyclo" shall denote any five or six membered monocyclic, nine or ten membered bicyclic or thirteen or fourteen membered tricyclic ring structure containing at least one heteroatom selected from the group consisting of N, O and S, optionally containing one to four additional heteroatoms, wherein the ring structure is saturated, partially unsaturated, aromatic or partially aromatic. The heterocyclyl group may be attached at any heteroatom or carbon atom which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropryanyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, triazinyl, triazolyl and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b] pyridinyl), dihydroisoindolyl, dihydroquinazolinyl (such as 3,4-dihydro-4-oxo-quinazolinyl), benzisoth iazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl and the like.

Exemplary tricyclic heterocylclic groups include phenoxazinyl, phenazinyl, phenothiazinyl, carbozolyl, perminidinyl, phenanthrolinyl, carbolinyl, naphthothienyl, thianthrenyl, and the like.

In the definition of Z, suitable examples of the

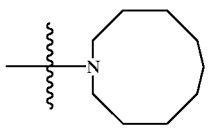

group include pyrazol-1-yl, imidazol-1-yl, pyrrol-1-yl, 1,2, 4-triazol-1-yl, 1,2,4-triazol-4-yl, 1,2,3-triazol-1-yl, aziridin-1-yl, pyrrolidin-1-yl, piperidin-1yl, piperazin-1-yl, morpholin-1-yl, 4-methyl-diazepin-1-yl, azepin-1-yl, diazepin-1-yl, 4-methyl-piperazin-1yl, and the like.

When a particular group is "substituted" (e.g., cycloalkyl, aryl, heterocyclyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylalkylaminocarbonylalkyl" substituent refers to a group of the formula

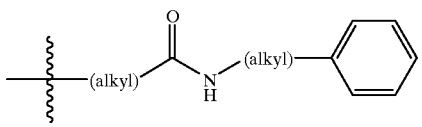

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of this invention, the term "chemical library" means a collection of molecules prepared by the method of the invention based on logical design by means of simultaneous or parallel chemical reactions. Each species of molecule in the library is referred to as a member of the library.

Abbreviations used in the specification, particularly the Schemes and Examples, are as follows:

| | |
|---|---|
| DCE = | 1,2-Dichloroethane |
| DCM = | Dichloromethane |
| DIPEA = | Diisopropylethylamine |
| DMF = | N,N-Dimethylformamide |
| $Et_2O$ = | Diethyl ether |
| ID# = | Compound ID number |
| MeOH = | Methanol |
| $Pd(PPh_3)_4$ = | Palladium, tetrakis(triphenylphosphine)- |
| TEA = | Triethylamine |
| TFA = | Trifluoroacetic acid |
| THF = | Tetrahydrofuran |
| THP = | Tetrahydropyran |

The compounds of formula (I) wherein $R^2$ is

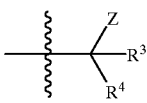

may be prepared on solid resin according to the process outlined in Scheme 1.

Scheme 1

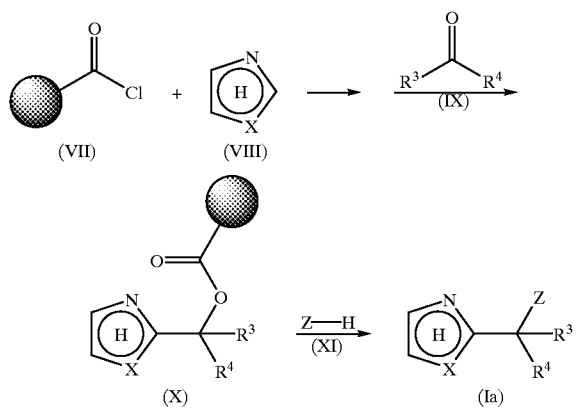

More specifically, a solid resin support of formula (VII), a resin support terminated with a carbonyl chloride functional group, a known compound or compound prepared by known methods (e.g. polystyrene-carbonylchloride resin from T. M. Fyles, C. C. Leznoff, J. Weatherston, *Can. J. Chem.* 1978, 56, 1031 and Meyers, at al., Molecular Diversity, 1, 13 (1995); or Reaction of NovaSyn® TG carboxy Resin from Calbiochem-Novabiochem Corp with oxalyl chloride;) is reacted with a compound of formula (VIII), a known compound or compound prepared by known methods, and then reacted with a compound of formula (IX), in a non-protic solvent such as acetonitrile, dioxane, THF, and the like, in the presence of a base such as TEA, and the like, at a temperature in the range of about 0° C. to about reflux, to form the corresponding compound of formula (X).

Where Z is a moiety other than H, the compound of formula (X) is then reacted with a compound of formula (XI), in the presence of an acid such as TFA, and the like, in a non-protic solvent such as acetonitrile, dioxane, THF, and the like, at a temperature in the range of about 0° C. to about reflux, resulting in cleavage of the resin support, to form the corresponding compound of formula (Ia).

When in the compound of formula (Ia) Z is H, the compound of formula (X) is reduced by transfer hydrogenation with a metal catalyst such as Pd(PPh$_3$)$_4$, and the like, in the presence of a source of transfer hydrogen such as triethylammonium formate, ammonium formate, and the like, wherein the source of transfer hydrogen is present in an amount equal to about 2 to 20 equivalents, preferably about 5 equivalents, in an organic solvent such as THF, dioxane, and the like, at a temperature in the range of about 40–110° C., preferably at about reflux temperature, to form the corresponding compound of formula (Ia).

Compounds of formula (II) wherein R$^2$ is

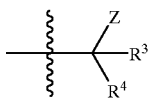

may be similarly prepared on solid resin according to the process outlined in Scheme 1, with appropriate substitution of a compound of formula (XII)

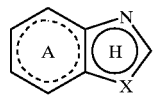

(XII)

for the compound of formula (VIII), to yield the corresponding compound of formula (IIa).

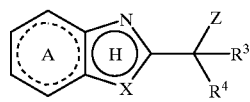

(IIa)

The following Examples are set forth to aid in the understanding of the invention, and are not intended and should not be construed to limit in any way the invention set forth in the claims which follow thereafter.

EXAMPLE A

Preparation of Polystyrene-Carboxylate Resin A

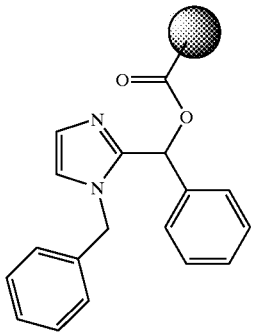

To a suspension of polystyrene-carbonylchloride resin (prepare from carboxypolystyrene by treatment with thionyl chloride, T. M. Fyles, C. C. Leznoff, J. Weatherston, *Can. J. Chem.* 1978, 56, 1031,) in THF is added 10 equivalents each of 1-benzylimidazole benzaldehyde, and then N,N-diisopropylethylamine. The mixture is shaken at room temperature for one to five days and washed five times with THF. The product resin is dried under vacuum overnight.

EXAMPLE B

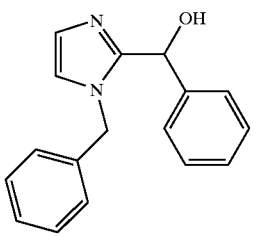

To a suspension of the resin prepared in as Example 1, in tetrahydrofuran, is added 20 equivalents of water and 5 equivalents of trifluoroacetic acid. The mixture is shaken one to five days at 65° C. and after cooling to room temperature is washed five times with tetrahydrofuran. The washes are concentrated to afford the product. The product is used as is or is purified by flash chromatography on silica eluted with methanol:methylene chloride mixtures to yield the purified product.

EXAMPLE C

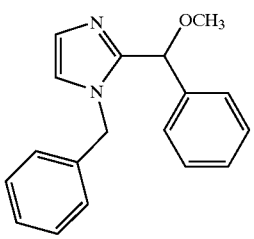

To a suspension of the resin prepared as in Example 1, in tetrahydrofuran, is added 20 equivalents of anhydrous methanol and 5 equivalents of trifluoroacetic acid. The mixture is shaken one to five days at 65° C. and after cooling to room temperature is washed five times with tetrahydrofuran. The washes are concentrated to afford the product. The product is used as is or is purified by flash chromatography on silica eluted with methanol:methylene chloride mixtures to yield the purified product.

EXAMPLE D

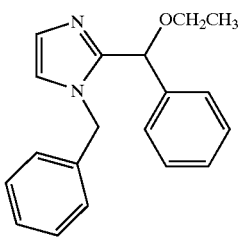

To a suspension of the resin prepared as in Example 1, in tetrahydrofuran, is added 20 equivalents of absolute ethanol and 5 equivalents of trifluoroacetic acid. The mixture is shaken one to five days at 65° C. and after cooling to room temperature is washed five times with tetrahydrofuran. The washes are concentrated to afford the product. The product is used as is or is purified by flash chromatography on silica eluted with methanol:methylene chloride mixtures to yield the purified product.

EXAMPLE E

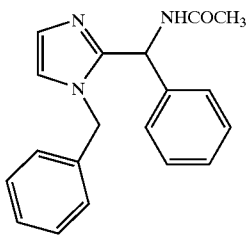

To a suspension of the resin prepared as in Example 1, in tetrahydrofuran, is added 20 equivalents of acetamide and 5 equivalents of trifluoroacetic acid. The mixture is shaken one to five days at 65° C. and after cooling to room temperature is washed five times with tetrahydrofuran. The washes are concentrated to afford the product. The product is purified by flash chromatography on silica eluted with methanol:methylene chloride mixtures to yield the purified product.

EXAMPLE F

To a suspension of the resin prepared as in Example 1, in tetrahydrofuran, is added 20 equivalents of methanesulfonamide and 5 equivalents of trifluoroacetic acid. The mixture is shaken one to five days at 65° C. and after cooling to room temperature is washed five times with tetrahydrofuran. The washes are concentrated to afford the product. The product is purified by flash chromatography on silica eluted with methanol:methylene chloride mixtures to yield the purified product.

EXAMPLE G

Preparation of Polystyrene-Carboxylate Resin B

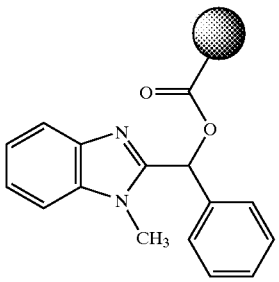

To a suspension of polystyrene-carbonylchloride resin (prepare from carboxypolystyrene by treatment with thionyl chloride, T. M. Fyles, C. C. Leznoff, J. Weatherston, *Can. J. Chem.* 1978, 56, 1031.) in THF is added 10 equivalents each of 1-methylbenzimidazole, benzaldehyde, and then N,N-diisopropylethylamine. The mixture is shaken at room temperature for one to five days and washed five times with THF. The resin product is dried under vacuum overnight.

EXAMPLE H

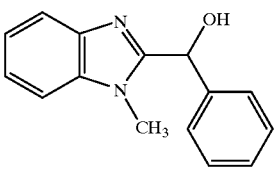

To a suspension of the resin prepared as in Example 7, in tetrahydrofuran, is added 20 equivalents of water and 5 equivalents of trifluoroacetic acid. The mixture is shaken one to five days at 65° C. and after cooling to room temperature is washed five times with tetrahydrofuran. The washes are concentrated to afford the product. The product is used as is or is purified by flash chromatography on silica eluted with methanol:methylene chloride mixtures to yield the purified product.

EXAMPLE I

Preparation of Polystyrene-Carboxylate Resin C

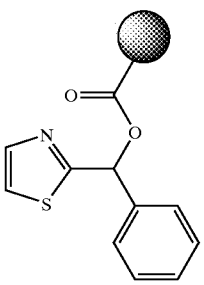

To a suspension of polystyrene-carbonylchloride resin (prepare from carboxypolystyrene by treatment with thionyl chloride, T. M. Fyles, C. C. Leznoff; J, Weatherston, *Can. J. Chem.* 1979, 56, 1031.) in THF is added 10 equivalents each of thiazole, benzaldehyde, and then N,N-diisopropylethylamine. The mixture is shaken at room temperature for one to five days and washed five times with THF. The resin product is dried under vacuum overnight.

EXAMPLE J

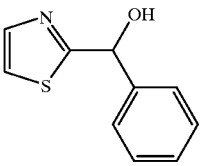

To a suspension of the resin prepared as in Example 9, in tetrahydrofuran, is added 20 equivalents of water and 5 equivalents of trifluoroacetic acid. The mixture is shaken one to five days at 65° C. and after cooling to room temperature is washed five times with tetrahydrofuran. The washes are concentrated to afford the product. The product is purified by flash chromatography on silica eluted with methanol:methylene chloride mixtures to yield the purified product.

EXAMPLE 1

Preparation of Polystyrene-Carboxylate Resin A

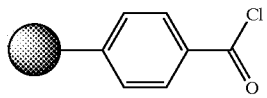

Method A:

To a suspension of polystyrene-carboxylate resin (2 g, loading 1.24 mmol/g from NovaBiochem) in dichloromethane (40 mL) was added oxalyl chloride (0.55 mL, 6.2 mmol) and DMF (0.5 mL) under nitrogen. The mixture was refluxed for 6 hours with a reflux condenser. After cooling to room temperature, the resin was washed five times with DCM to yield the title product, the polystyrene-carbonylchloride resin A.

Method B:

To a suspension of polystyrene-carboxylate resin (2 g loading 1.24 mmol from NovaBiochem) in toluene (40 mL) was added oxalyl chloride (0.55 mL, 6.2 mmol) under nitrogen. The mixture was heated for 6 hours at 60° C. with a reflux condenser. After cooling to room temperature, the resin was washed two times with toluene and three times with DCM to yield the title compound, the polystyrene-carbonylchloride resin A.

EXAMPLE 2

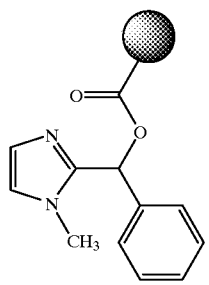

To a suspension of polystyrene-carbonylchloride resin A (prepared as in Example 1) in tetrahydrofuran was added 5 equivalents of methylimidazolyl, 10 equivalents benzaldehyde, and then 10 equivlanets of N,N-diisopropylethylamine. The mixture was shaken at room temperature for 24 hours and washed with DCM. The product resin B was dried under vacuum overnight.

EXAMPLE 3

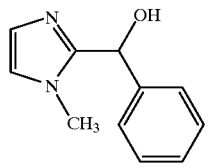

To a suspension of the resin prepared as in Example 2, in tetrahydrofuran were added 20 equivalents of water and 10 equivalents of trifluoroacetic acid. The mixture was shaken for 24 hours at 65° C. and after cooling to room temperature was washed with tetrahydrofuran, DCM and methanol. The washes were concentrated to afford the product. The product was purified by flash chromatography on silica eluted with methanol:ethyl acetate mixtures to yield the purified product.

LC/MS (ESP) m/z 189 (MH$^+$)

EXAMPLE 4

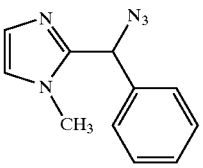

To a suspension of the resin prepared as in Example 2, in DMF, was added 10 equivalents of NaN$_3$ and 5 equivalents of BF$_3$.Et$_2$O. The mixture was shaken for 24 hours at 70° C. and after cooling to room temperature was washed with DCM and methanol. The washes were concentrated to afford the product. The product was purified by flash chromatography on silica eluted with methanol:ethyl acetate mixtures to yield the purified product.

LC/MS (ESP) m/z 214 (MH$^+$)

EXAMPLE 5

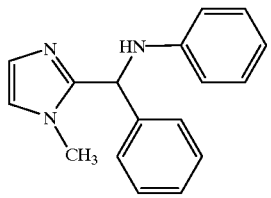

To a suspension of the resin prepared as in Example 2, in tetrahydrofuran were added 10 equivalents of aniline and 6 equivalents of trifluoroacetic acid. The mixture was shaken for 24 hours at 65° C. and after cooling to room temperature was washed five times with tetrahydrofuran, DCM and MeOH. The washes were concentrated to afford the product. The product was purified by flash chromatography on silica eluted with ethyl acetate and hexane mixtures to yield the purified product.

LC/MS (ESP) m/z 264 (MH$^+$).

EXAMPLE 5

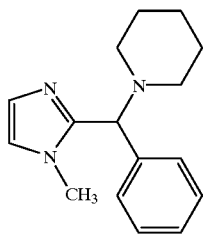

To a suspension of the resin prepared as in Example 2, in tetrahydropyran, were added 10 equivalents of piperidine, 9 equivalents of trifluoroacetic acid and 1.5 equivalents of BF$_3$.Et$_2$O. The mixture was shaken 24 hours and after cooling to room temperature was washed with tetrahydrofuran, DCM and MeOH. The washes were concentrated to afford the product.

LC/MS (ESP) mlz 256 (MH$^+$).

EXAMPLE 7

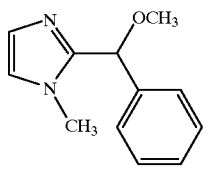

To a suspension of the resin prepared in as Example 2, in tetrahydrofuran, were added 20 equivalents of methanol and 10 equivalents of trifluoroacetic acid. The mixture was shaken 24 hours at 65° C. and after cooling to room temperature was washed with DCM and MeOH. The washes were concentrated to afford the product.

LC/MS (ESP) m/z 203 (MH$^+$).

EXAMPLE 8

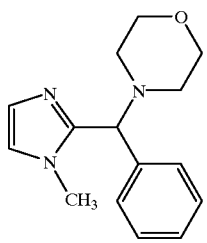

To a suspension of the resin prepared as in Example 2, in tetrahydropyran, were added 10 equivalents of morpholine, 9 equivalents of trifluoroacetic acid and 1.5 equivalents of BF$_3$.Et$_2$O. The mixture was shaken 24 hours at 70° C. and after cooling to room temperature was washed with tetrahydrofuran, DCM and MeOH. The washes were concentrated to afford the product.

LC/MS (ESP) m/z 258 (MH$^+$).

EXAMPLES 9–13

Following the procedures described in Examples 3 to 8 above, selected compounds of the present invention were prepared as listed in Table 1

TABLE 1

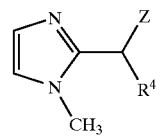

| ID # | Z | R$^4$ | Measured Mass spec (MH$^+$) |
|---|---|---|---|
| 9 | phenyloxy | phenyl | 265 |
| 10 | 4-methyl-piperazin-1-yl | phenyl | 271 |

TABLE 1-continued

| ID # | Z | R$^4$ | Measured Mass spec (MH$^+$) |
|---|---|---|---|
| 11 | methoxyamino | phenyl | 218 |
| 12 | (2-hydroxyethyl)thio | phenyl | 249 |
| 13 | (2-hydroxyethyl)amino | phenyl | 232 |

EXAMPLE 14

Preparation of Polystyrene-Carboxylate Resin C

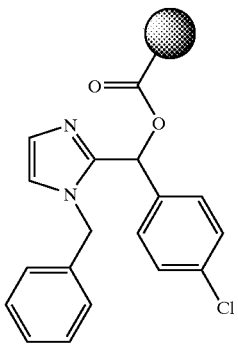

To a polystyrene-carbonylate resin loaded in ACT 496 MOS blocks (Advanced Chem Tech, Louisville, Ky., USA) was added 5 equivalents of oxalyl chloride in toluene. The mixtures were shaken at about 40° C. for 20 hours. The reaction well was emptied, and washed with toluene and dichloromethane to yield the polystyrene-carbonylchloride resin.

To the well loaded with the polystyrene-carbonylchloride resin, 6 equivalents of 4-chlorobenzaldehyde in dichloromethane, 3 equivalents of 1-benzylimidazole and 6 equivalents of N,N-diisopropylethylamine in dichloromethane were added consecutively. The mixture was shaken at room temperature for 48 hours and washed with DCM to yield the title compound, the polystyrene-carbonylate resin C.

EXAMPLE 15

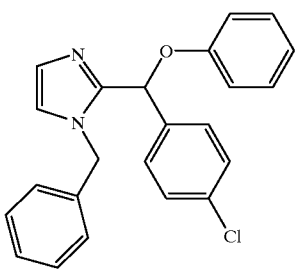

To the resin prepared as in Example 8 above were added 5 equivalents of phenol in tetrahydropyran, 4 equivalents of trifluoroacetic acid and 1.5 equivalents of BF$_3$.Et$_2$O in tetrahydropyran. The mixture was shaken 24 hours at 50° C. and after cooling to room temperature was washed with tetrahydrofuran, DCM and methanol. The washes were concentrated to yield the title product as a solid. MS (ESP) MH⁺ 376.

EXAMPLE 16–127

Following the procedures described in Examples 14 and 15 above, selected compounds of the present invention were prepared using the ACT 496 MOS robot (Advanced Chem Tech, Louisville, Ky., USA) as listed in Table 2 and 3.

TABLE 2

| ID # | X | Z | R⁴ | Meas. MW |
|---|---|---|---|---|
| 16 | 1-benzyl-imidazol-2-yl | Piperidin-1-yl | 4-chlorophenyl | 281 (M⁺ loss of $C_5H_{10}N$) |
| 17 | 1-benzyl-imidazol-2-yl | 4-methyl-piperazin-1-yl | 4-chlorophenyl | 381 |
| 18 | 1-methyl-5-chloro-imidazol-2-yl | 4-morpholin-1-yl | 4-chlorophenyl | 239 (M⁺ loss of $C_4H_8ON$) |
| 19 | 1-methyl-5-chloro-imidazol-2-yl | 4-methyl-piperazin-1-yl | 4-chlorophenyl | 339 |
| 20 | 4-benzyl-1,2,4-triazol-3-yl | 4-morpholin-1-yl | 4-chlorophenyl | 381 (M Na⁺) |
| 21 | 4-benzyl-1,2,4-triazol-3-yl | 4-methyl-piperazin-1-yl | 4-chlorophenyl | 404 (M Na⁺) |
| 23 | thiazol-2-yl | 4-morpholin-1-yl | 4-chlorophenyl | 317 (M Na⁺) |
| 24 | thiazol-2-yl | 4-methyl-piperazin-1-yl | 4-chlorophenyl | 208 (M⁺ loss of $C_5H_{11}N_2$) |
| 25 | 4-methyl-5-vinyl-thiazol-2-yl | 4-methyl-piperazin-1-yl | 4-chlorophenyl | 248 (M⁺ loss of $C_5H_{11}N_2$) |
| 26 | 1-benzyl-imidazol-2-yl | 4-morpholin-1-yl | 4-methoxyphenyl | 364 |
| 27 | 1-benzyl-imidazol-2-yl | 4-methyl-piperazin-1-yl | 4-methoxyphenyl | 377 |
| 28 | 1-methyl-5-chloro-imidazol-2-yl | 4-morpholin-1-yl | 4-methoxyphenyl | 235 (M⁺ loss of $C_4H_8ON$) |
| 29 | 1-methyl-5-chloro-imidazol-2-yl | 4-methyl-piperazin-1-yl | 4-methoxyphenyl | 335 |
| 32 | thiazol-2-yl | 4-morpholin-1-yl | 4-methoxyphenyl | 204 (M⁺ loss of $C_4H_8ON$) |
| 33 | thiazol-2-yl | 4-methyl-piperazin-1-yl | 4-methoxyphenyl | 304 |
| 34 | 4-methyl-5-vinyl-thiazol-2-yl | 4-morpholin-1-yl | 4-methoxyphenyl | 331 |
| 35 | 4-methyl-5-vinyl-thiazol-2-yl | 4-methyl-piperazin-1-yl | 4-methoxyphenyl | 344 |
| 36 | 1-benzyl-imidazol-2-yl | 4-morpholin-1-yl | vinyl | 284 |
| 37 | 1-benzyl-imidazol-2-yl | 4-methyl-piperazin-1-yl | vinyl | 297 |
| 38 | 1-methyl-5-chloro-imidazol-2-yl | 4-morpholin-1-yl | vinyl | 242 |
| 39 | 4-benzyl-1,2,4-triazol-3-yl | 4-morpholin-1-yl | vinyl | 285 |
| 40 | 4-benzyl-1,2,4-triazol-3-yl | 4-methyl-piperazin-1-yl | vinyl | 298 |
| 43 | thiazol-2-yl | 4-morpholin-1-yl | vinyl | 211 |
| 44 | thiazol-2-yl | 4-methyl-piperazin-1-yl | vinyl | 224 |
| 45 | 4-methyl-5-vinyl-thiazol-2-yl | 4-morpholin-1-yl | vinyl | 251 |
| 46 | 4-methyl-5-vinyl-thiazol-2-yl | 4-methyl-piperazin-1-yl | vinyl | 264 |
| 47 | 1-benzyl-imidazol-2-yl | 4-morpholin-1-yl | 2-pyridyl | 248 (M⁺ loss of $C_4H_8ON$) |
| 48 | 1-benzyl-imidazol-2-yl | 4-methyl-piperazin-1-yl | 2-pyridyl | 348 |
| 49 | 1-methyl-5-chloro-imidazol-2-yl | 4-morpholin-1-yl | 2-pyridyl | 206 (M⁺ loss of $C_4H_8ON$) |
| 50 | 1-methyl-5-chloro-imidazol-2-yl | 4-methyl-piperazin-1-yl | 2-pyridyl | 206 (M⁺ loss of $C_5H_{11}N_2$) |
| 51 | 4-benzyl-1,2,4-triazol-3-yl | 4-morpholin-1-yl | 2-pyridyl | 358 (M Na⁺) |
| 52 | 4-benzyl-1,2,4-triazol-3-yl | 4-methyl-piperazin-1-yl | 2-pyridyl | 349 |
| 53 | thiazol-2-yl | 4-morpholin-1-yl | 1-methylpyrrol-2-yl | 286 (M Na⁺) |
| 54 | thiazol-2-yl | 4-methyl-piperazin-1-yl | 1-methylpyrrol-2-yl | 299 (M Na⁺) |
| 55 | 1-benzyl-imidazol-2-yl | 4-morpholin-1-yl | thiophen-3-yl | 340 |
| 56 | 1-benzyl-imidazol-2-yl | 4-methyl-piperazin-1-yl | thiophen-3-yl | 353 |
| 57 | 1-methyl-5-chloro-imidazol-2-yl | 4-morpholin-1-yl | thiophen-3-yl | 398 |
| 58 | 1-methyl-5-chloro-imidazol-2-yl | 4-methyl-piperazin-1-yl | thiophen-3-yl | 311 |
| 59 | 4-benzyl-1,2,4-triazol-3-yl | 4-morpholin-1-yl | thiophen-3-yl | 341 |
| 60 | 4-benzyl-1,2,4-triazol-3-yl | 4-methyl-piperazin-1-yl | thiophen-3-yl | 254 (M⁺ loss of $C_5H_{11}N_2$) |
| 63 | thiazol-2-yl | 4-morpholin-1-yl | thiophen-3-yl | 180 |
| 64 | thiazol-2-yl | 4-methyl-piperazin-1-yl | thiophen-3-yl | 280 |
| 67 | thiazol-2-yl | 4-morpholin-1-yl | phenylethynyl | 285 |
| 68 | 4-methyl-5-vinyl-thiazol-2-yl | 4-morpholin-1-yl | phenylethynyl | 325 |
| 69 | 4-methyl-5-vinyl-thiazol-2-yl | 4-methyl-piperazin-1-yl | phenylethynyl | 338 |
| 70 | 1-benzyl-imidazol-2-yl | phenyloxy | 4-chlorophenyl | 375 |
| 71 | 1-benzyl-imidazol-2-yl | Piperidin-1-yl | 4-methoxyphenyl | 368 |
| 72 | 1-benzyl-imidazol-2-yl | 2-pyridylamino | 4-chlorophenyl | 375 |
| 73 | thiazol-2-yl | 2-hydroxy ethylthio | 4-chlorophenyl | 285 |
| 74 | 1-benzyl-imidazol-2-yl | phenyloxy | 4-methoxyphenyl | 371 |
| 75 | 1-benzyl-imidazol-2-yl | Piperidin-1-yl | 4-methoxyphenyl | 362 |
| 76 | 1-benzyl-imidazol-2-yl | 2-hydroxy ethylthio | 4-methoxyphenyl | 277 (M⁺ loss of $C_2H_6NS$) |
| 77 | 1-benzyl-imidazol-2-yl | 2-pyridylamino | 4-methoxyphenyl | 371 |
| 78 | thiazol-2-yl | Piperidin-1-yl | 2-pyridyl | 260 |
| 79 | thiazol-2-yl | 2-pyridylamino | 2-pyridyl | 269 |
| 80 | 1-benzyl-imidazol-2-yl | phenyloxy | 1-methylpyrrol-2-yl | 344 |
| 81 | 1-benzyl-imidazol-2-yl | phenyloxy | thiophen-3-yl | 347 |
| 82 | 1-benzyl-imidazol-2-yl | Piperidin-1-yl | thiophen-3-yl | 338 |
| 83 | 1-benzyl-imidazol-2-yl | 2-hydroxy ethylthio | thiophen-3-yl | 253 (M⁺ loss of $C_2H_6NS$) |
| 84 | 1-benzyl-imidazol-2-yl | 2-pyridylamino | thiophen-3-yl | 347 |
| 85 | thiazol-2-yl | phenyloxy | thiophen-3-yl | 274 |
| 86 | thiazol-2-yl | 2-hydroxy ethylthio | thiophen-3-yl | 257 |

TABLE 2-continued

| ID # | X | Z | R⁴ | Meas. MW | |
|---|---|---|---|---|---|
| 87 | 1-benzyl-imidazol-2-yl | phenyloxy | 3,5-di(trifluoro methyl)phenyl | 477 | |
| 88 | 1-benzyl-imidazol-2-yl | Piperidin-1-yl | 3,5-di(trifluoro methyl)phenyl | 468 | |
| 89 | 1-benzyl-imidazol-2-yl | 2-hydroxy ethylthio | 3,5-di(trifluoro methyl)phenyl | 383 | |
| 90 | 1-benzyl-imidazol-2-yl | 2-pyridylamino | 3,5-di(trifluoro methyl)phenyl | 477 | |
| 91 | thiazol-2-yl | phenyloxy | 1-methylindol-3-yl | 321 | |
| 92 | thiazol-2-yl | 2-pyridylamino | 1-methylindol-3-yl | 321 | |
| 93 | 1-benzyl-imidazol-2-yl | phenyloxy | 4-biphenyl | 417 | |
| 94 | 1-benzyl-imidazol-2-yl | Piperidin-1-yl | 4-biphenyl | 323 | |
| 95 | 1-benzyl-imidazol-2-yl | 2-hydroxy ethylthio | 4-biphenyl | 323 | |
| 96 | 1-benzyl-imidazol-2-yl | 2-pyridylamino | 4-biphenyl | 417 | |
| 97 | 1-benzyl-imidazol-2-yl | phenyloxy | 1-phenylpyrazol-4-yl | 407 | |
| 98 | 1-benzyl-imidazol-2-yl | Piperidin-1-yl | 1-phenylpyrazol-4-yl | 398 | |
| 99 | 1-benzyl-imidazol-2-yl | 2-hydroxy ethylthio | 1-phenylpyrazol-4-yl | 313 | (M⁺ loss of $C_2H_6NS$) |
| 100 | 1-benzyl-imidazol-2-yl | 2-pyridylamino | 1-phenylpyrazol-4-yl | 407 | |
| 101 | thiazol-2-yl | phenyloxy | 1-phenylpyrazol-4-yl | 334 | |
| 102 | thiazol-2-yl | Piperidin-1-yl | 1-phenylpyrazol-4-yl | 240 | (M⁺ loss of $C_5H_{10}N$) |
| 103 | thiazol-2-yl | 2-hydroxy ethylthio | 1-phenylpyrazol-4-yl | 317 | |
| 104 | 1-benzyl-imidazol-2-yl | phenyloxy | 3-benzyloxy-phenyl | 447 | |
| 105 | 1-benzyl-imidazol-2-yl | Piperidin-1-yl | 3-benzyloxy phenyl | 438 | |
| 106 | 1-benzyl-imidazol-2-yl | 2-hydroxy ethylthio | 3-benzyloxy-phenyl | 353 | (M⁺ loss of $C_2H_6NS$) |
| 107 | 1-benzyl-imidazol-2-yl | 2-pyridylamino | 3-benzyloxy-phenyl | 447 | |
| 108 | 1-benzyl-imidazol-2-yl | phenyloxy | 4-chlorophenyl | 376 | |
| 109 | 1-benzyl-imidazol-2-yl | phenylamino | 4-chlorophenyl | 375 | |
| 110 | 1-methyl-5-chloro-imidazol-2-yl | phenyloxy | 4-chlorophenyl | 333 | |
| 112 | 1-benzyl-imidazol-2-yl | phenylamino | 4-methoxyphenyl | 370 | |
| 114 | 1-benzyl-imidazol-2-yl | phenylamino | 2-pyridyl | 341 | |
| 115 | 1-methyl-5-chloro-imidazol-2-yl | phenylamino | 2-pyridyl | 206 | (M⁺ loss of $C_6H_6N$) |
| 117 | 1-benzyl-imidazol-2-yl | phenylamino | thiophen-3-yl | 346 | |
| 118 | 1-methyl-5-chloro-imidazol-2-yl | phenyloxy | thiophen-3-yl | 306 | |
| 119 | 1-methyl-5-chloro-imidazol-2-yl | phenylamino | thiophen-3-yl | 321 | |
| 121 | 4-methyl-5-vinyl-thiazol-2-yl | 4-morpholin-1-yl | thiophen-3-yl | 307 | |
| 122 | 4-methyl-5-vinyl-thiazol-2-yl | 4-methyl-piperazin-1-yl | thiophen-3-yl | 320 | |
| 123 | 1-benzyl-imidazol-2-yl | 4-morpholin-1-yl | phenylethynyl | 358 | |
| 124 | 1-benzyl-imidazol-2-yl | 4-methyl-piperazin-1-yl | phenylethynyl | 371 | |
| 125 | 1-methyl-5-chloro-imidazol-2-yl | 4-morpholin-1-yl | phenylethynyl | 316 | |
| 126 | 1-methyl-5-chloro-imidazol-2-yl | 4-methyl-piperazin-1-yl | phenylethynyl | 329 | |
| 127 | 4-benzyl-1,2,4-triazol-3-yl | 4-methyl-piperazin-1-yl | phenylethynyl | 272 | (M⁺ loss of $C_5H_{11}N_2$) |

TABLE 3

| ID # | X | Z | R4 | Meas. MW | |
|---|---|---|---|---|---|
| 22 | 1-methyl-benzimidazol-2-yl | 4-methyl-piperazin-1-yl | 4-chlorophenyl | 255 | (M⁺ loss of $C_5H_{11}N_2$) |
| 30 | 1-methyl-benzimidazol-2-yl | 4-morpholin-1-yl | 4-methoxyphenyl | 251 | (M⁺ loss of $C_4H_8ON$) |
| 31 | 1-methyl-benzimidazol-2-yl | 4-methyl-piperazin-1-yl | 4-methoxyphenyl | 251 | (M⁺ loss of $C_4H_{11}N_2$) |
| 41 | 1-methyl-benzimidazol-2-yl | 4-morpholin-1-yl | vinyl | 258 | |
| 42 | 1-methyl-benzimidazol-2-yl | 4-methyl-piperazin-1-yl | vinyl | 271 | |
| 61 | 1-methyl-benzimidazol-2-yl | 4-morpholin-1-yl | thiophen-3-yl | 314 | |
| 62 | 1-methyl-benzimidazol-2-yl | 4-methyl-piperazin-1-yl | thiophen-3-yl | 327 | |
| 65 | 1-methyl-benzimidazol-2-yl | 4-morpholin-1-yl | phenylethynyl | 332 | |
| 66 | 1-methyl-benzimidazol-2-yl | 4-methyl-piperazin-1-yl | phenylethynyl | 345 | |
| 111 | 1-methyl-benzimidazol-2-yl | phenylamino | 4-chlorophenyl | 371 | |
| 113 | 1-methyl-benzimidazol-2-yl | phenylamino | 4-trifluoromethyl phenyl | 248 | (M⁺ loss of $C_6H_6N$) |
| 116 | 1-methyl-benzimidazol-2-yl | phenylamino | 1-methylpyrrol-2-yl | 347 | |
| 120 | 1-methyl-benzimidazol-2-yl | phenylamino | thiophen-3-yl | 365 | |

While some the previous examples describe the purification of reaction products by flash chromatography, these reaction products can also be purified in a high-throughput mode using high-throughput reverse-phase or high-throughput normal phase HPLC instruments, thereby, increasing the efficiency of compounds library syntheses.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of synthesizing highly substituted azole compounds of formula (I):

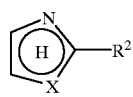

(I)

wherein

X is selected from the group consisting of NH, $NR^A$ and S;

represents a 5 membered aromatic ring structure optionally containing one to two additional heteroatoms selected horn the group consisting of N, O and S;

wherein the additional heteroatoms are not at the attachment point of the $R^2$ group;

wherein the 5 membered ring remains aromatic in nature;

wherein the 5 membered ring is optionally substituted with one to three substituents independently selected from the group consisting of halogen, hydroxy, alkyl, alkenyl, halogenated alkyl, cycloalkyl, alkoxy, aryl, aralkyl, heterocyclyl, amino, mono- or di-alkyl amino, mono- or di-cycloalkylamino, mono- or di-arylamino, mono- or di-aralkylamino, cyano, nitro, —COOR, —COR, —$SO_2R$ end —$CONR^bR^C$; wherein the cycloalkyl, aryl or heterocyclyl may be further optionally substituted with one or more substituents wherein the one or more substituents are independently selected from halogen, hydroxy, alkyl, halogenated alkyl, alkoxy, amino, mono- or di-alkyl amino, cyano or nitro;

$R^2$ is

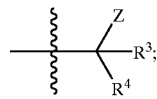

Z is selected from the group consisting of hydrogen, —OH, —OR, —$NR^AR^B$, $N(R^A)OR^B$, —SR, —CN, —$N_3$, and

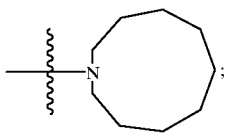

wherein

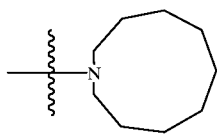

represents a three to eight membered heterocyclyl group bound at the N atom, wherein the heterocyclyl group is saturated, partially unsaturated or aromatic; when the heterocyclyl group is a saturated six to eight membered heterocyclyl, the heterocyclyl group may optionally contains a group selected from O, CHR, NR, S, SO, or $SO_2$, provided that that the group is separated from the N atom by at least two carbon atoms; and wherein the heterocyclyl group is optionally substituted with one or more substituents independently selected from R;

$R^3$ is hydrogen;

$R^4$ is selected from the group consisting of aryl, aralkyl, alkenyl, alkynyl, aralkynyl, and heterocyclyl; wherein the, alkenyl, alkynyl, aryl, aralkyl, aralkynyl, or heterocyclyl may be optionally substituted with one or more substituents independently selected from halogen, hydroxy, alkyl, halogenated alkyl, aryl, alkoxy, aryloxy, amino, mono- or di-alkyl amino, mono- or di-cycloalkylamino, mono- or di-arylamino, mono- or di-aralkylamino, cyano or nitro;

where R is selected from the group consisting of alkyl, aryl, aralkyl, cycloalkyl, fluorinated alkyl and heterocycle; wherein the alkyl, aryl, aralkyl or heterocycle may be optionally substituted with one or more substituents independently selected from halogen, hydroxy, alkyl, halogenated alkyl, alkoxy, amino, mono- or di-alkyl amino, cyano or nitro; where $R^A$ is selected from the group consisting of hydrogen, —R, —COOR, —COR, —$SO_2R$ and —$CONR^BR^C$ and

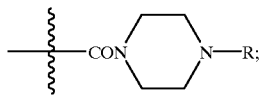

where $R^B$ and $R^C$ are independently selected form the group consisting of hydrogen, alkyl, aryl, aralkyl, cycloalkyl, fluorinated alkyl and heterocycle; wherein the aryl, aralkyl or heterocycle may be optionally substituted with one or more substituents independently selected from halogen, hydroxy, alkyl, halogenated alkyl, alkoxy, amino, mono- or di-alkyl amino, mono- or di-cycloalkylamino, mono- or di-arylamino, mono- or di-aralkylamino, cyano or nitro; or are joined together to form a 4 to 8 membered heterocyclyl ring structure;

which method comprises:

a) preparing a compound of the formula (III) on a solid support resin,

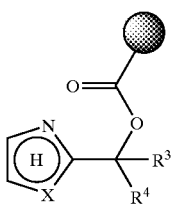 (III)

by reacting a carbonyl chloride substituted resin of formula (VII) with an aromatic heterocycle of formula (VIII) and an aldehyde of formula (IX)

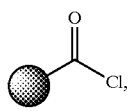 (VII)

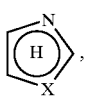 (VIII)

 (IX)

wherein $R^3$ and $R^4$ are as described above;

b) cleaving the compound from the solid support resin by nucleophilic substitution to yield the corresponding compound of formula (I);

c) optionally further substituting the compound of formula (I) via alkylation reactions in solution phase.

2. The process of claim 1, wherein

is selected from the group consisting of imidazolyl, substituted imidazolyl (wherein the substituents on the imidazolyl group are one to two independently selected from halogen, alkyl, alkenyl, aryl or aralkyl), triazolyl, substituted triazolyl (wherein the substituent on the triazolyl group is aralkyl), thiazolyl and substituted thiazolyl (wherein the substituents on the thiazolyl group are one to two independently selected from halogen, alkyl and alkenyl);

$R^2$ is

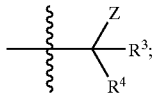

Z is selected from the group consisting of —OH, —O-(alkyl), —O-(aryl), —N₃, —NH(alkoxy), —NH-(alkyl), —NH-alkyl-OH), —NH(aryl), —NH-(heterocyclyl), —S-(alkyl), —S-(alkyl-OH) and

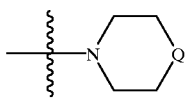

(wherein Q is selected from CH₂, NH, N-alkyl or O);

$R^3$ hydrogen; and $R^4$ is selected from the group consisting of alkenyl, phenyl-alkynyl, aryl, substituted aryl (wherein the substituents on the aryl group are one to two independently selected from halogen, alkyl, alkoxy, trifluoromethyl, —O-aryl or —O-aralkyl), aralkyl, biphenyl, heterocyclyl and substituted heterocyclyl (wherein the substituent on the heterocyclyl group is selected from alkyl, or aryl).

3. The process of claim 2 wherein

is selected from the group consisting of 1-methyl-inidazol-2-yl, 1-benzyl-imidazol-2-yl, 1-methyl-5-chloro-imidazol-2-yl, 4-methyl-5-vinyl-thiazol-2-yl, 4-benzyl-1,2,4-triazol-3-yl and thiazol-2-yl;

$R^2$ is selected from the group consisting of

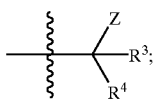

Z is selected from the group consisting of —OH, —OCH₃, —O-phenyl, —N₃, —NH(OCH₃), —NH—CH₂CH₂OH, —NH(phenyl), —NH-(2-pyridyl), —S—CH₂CH₂—OH, piperidin-1-yl, 4-morpholin-1-yl and 4-methyl-piperazin-1yl;

$R^3$ hydrogen; and $R^4$ is selected from the group consisting of vinyl, phenyl, 4-chlorophenyl, 4-methoxyphenyl, 2-pyridyl, 1-methyl-pyrrol-2-yl, thiophen-3-yl, 3,5-di(trifluoromethyl)phenyl, 1-methylindol-3-yl, 4-biphenyl, 1-phenyl-pyrazol-4-yl, 3-benzyloxy-phenyl and phenylethynyl.

* * * * *